United States Patent [19]
Craik et al.

[11] Patent Number: 6,165,794
[45] Date of Patent: *Dec. 26, 2000

[54] SUPPRESSION OF PROTEOLYTIC ACTIVITY BY DYSFUNCTIONAL PROTEASE FORMATION

[75] Inventors: Charles S. Craik; Lilia M. Babé; Jason R. Rosé, all of San Francisco, Calif.

[73] Assignee: The Regents of the University of California, Oakland, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/338,056

[22] Filed: Nov. 10, 1994

[51] Int. Cl.[7] .......................... C21N 15/49; C21N 15/86; C21N 15/867; C07H 21/00

[52] U.S. Cl. .................. 435/455; 435/320.1; 435/456; 536/23.1; 536/23.72

[58] Field of Search .......................... 435/240.2, 172.3, 435/320.2, 235.1, 236, 212, 219; 536/23.2, 23.72; 935/14, 22, 32

[56] References Cited

FOREIGN PATENT DOCUMENTS

WO 90/11359  10/1990  WIPO .

OTHER PUBLICATIONS

Loeb et al. 1989 Nature 340: 397–400.
Webster's II New Riverside University Dictionary, 1984, Houghton Mifflin Company, Boston, MA p. 997.
Watson et al., 1987, in: Molecular Biology Of The Gene, fourth edition, Benjamin–Cummings Publ. Co., Menlo Park, Ca p. 313.
Singleton et al., in 1987, in: Dictionary Of Microbiology And Molecular Biology, second edition, John Wiley and Sons, Chichester, GB, pp. 753–756.
Navia et al., 1989, Nature, 337: 615–620.
Feinberg, Mark B., et al. (1992) "Intracellular Immunization: Trans–Dominant Mutants of HIV Gene Products as Tools for the Study and Interruption of Viral Replication", *Aids Research and Human Retroviruses*, 8(6):1013–1022.
Babe, Lilia M., et al. (1992) "Synthetic 'interface' peptides alter dimeric assembly of the HIV 1 and 2 Proteases", *Protein Science* 1:1244–1253.
Babe, Lilia M., et al. (1991) "Inhibition of HIV Protease Activity by Heterodimer Formation", *Biochemistry* 30:106–111.
Rose, Jason R., et al. (1993) "Regulation of Autoproteolysis of the HIV–1 and HIV–2 Proteases with Engineered Amino Acid Substitutions", *The Journal of Biological Chemistry*, 268(16):11939–11945.
Wlodawer, Alexander, et al. (1989) "Conserved Folding in Retroviral Proteases: Crystal Structure of a Synthetic HIV–1 Protease", *Science*, 245:616–621.
Page, Kathleen, A., et al. (1990) "Construction and Use of a Human Immunodeficiency Virus Vector for Analysis of Virus Infectivity", *Journal of Virology*, 64(11):5270–5276.
Trono, Didier, et al. (1989) "HIV–1 Gag Mutants Can Dominantly Interfere with the Replication of the Wild–Type Virus", *Cell*, 59:113–120.

*Primary Examiner*—Scott D. Priebe
*Attorney, Agent, or Firm*—Townsend & Townsend & Crew LLP

[57] ABSTRACT

The present invention provides recombinant vectors comprising polynucleotides encoding defective monomers of HIV (e.g., HIV-1 or HIV-2) protease which are used to interfere with viral maturation. The defective monomers result in the formation of inactive protease heterodimers and thus inhibit the polyprotein processing events that are essential for viral maturation and infectivity.

6 Claims, 3 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:

```
            (A) LENGTH: 99 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..99
            (D) OTHER INFORMATION: /note= "HIV protease monomer"

(xi) SEQUENCE DESCRIPTION: SEQ ID NO:1:

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
                20                  25                  30

Leu Glu Glu Met Asn Leu Pro Gly Arg Trp Lys Pro Lys Met Ile Gly
            35                  40                  45

Gly Ile Gly Gly Phe Ile Lys Val Arg Gln Tyr Asp Gln Ile Leu Ile
        50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe (2) INFORMATION FOR SEQ ID NO:2:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..10
            (D) OTHER INFORMATION: /note= "residues 151-160 of the
                                   sequence of the natural HIV-1 gag-pol
                                   polyprotein represent the junction
                                   between protease and reverse
                                   transcriptase"

(xi) SEQUENCE DESCRIPTION: SEQ ID NO:2:

Ala Thr Leu Asn Phe Pro Ile Ser Pro Trp
1               5                   10
```

SUPPRESSION OF PROTEOLYTIC ACTIVITY BY DYSFUNCTIONAL PROTEASE FORMATION

BACKGROUND OF THE INVENTION

The present invention relates to compositions and methods for inhibiting activity of multimeric enzymes. In particular, it relates to inhibition of proteases by formation of dysfunctional protease multimers.

Protein structure is typically discussed in terms of four levels. The primary structure is the amino acid sequence; the secondary structure is any regular local structure of linear segment, such as an α-helix; the tertiary structure is the overall topology of the folded polypeptide chain; and the quaternary structure is the aggregation of single polypeptides or subunits to form a functional molecule.

Many proteins exist as assemblies of two or more polypeptide chains, which may be identical or different. Complex interactions between the subunits are required to produce a functional protein. For example, multimeric enzymes can be rendered inactive, if the interaction of the monomers is disrupted.

Multimeric enzymes of particular interest to the present invention are multimeric proteases. Inhibition of protease activity may be useful in a number of contexts. For example, inhibition of retroviral proteases, which are critical to retroviral maturation and infectivity, can be used to inhibit retroviral infection.

Retroviruses are those viruses which have a single stranded RNA genome, a lipid envelope, and encode an RNA-dependent deoxyribonucleic acid (DNA) polymerase, known as reverse transcriptase. During their life cycle, the RNA genome is reverse transcribed into a DNA copy which is integrated into the genome of the host cell. A number of retroviruses cause disease states in humans. These include the lentiviruses, human immunodeficiency viruses (HIV-1 and HIV-2), which cause acquired immune deficiency syndrome (AIDS), and the oncoviruses, human T-cell lymphotrophic viruses I and II which cause T cell leukemias.

Retroviruses, such as HIV-1, encode aspartic proteases that process polyprotein precursors into viral structural proteins and replicative enzymes that are essential for viral proliferation. Autoprocessing of the protease from the gag/pol polyprotein precursor results in the release of the protease and the generation of mature structural and enzymatic proteins derived from the gag and gag/pol polyproteins.

Studies of the crystal structure of HIV proteases (Navia, et al, *Nature* 337:615–620 (1989); Wlodawer, et al., *Science* 245:616–621 (1989)) have confirmed the homodimeric nature of these enzymes. Assembly of the two HIV protease monomers results in a dimer of approximately 22KD and generates an active site at the interface of the subunits.

These X-ray crystallographic studies have also defined regions of interaction between the monomers. Each monomer contributes half of the active site, which includes two catalytic aspartic acids as well as threonine/serine and glycine residues which are conserved among all aspartyl proteases for their structural role in maintaining active site geometry. The two N-termini and two C-termini of the individual monomers form β-strands that interdigitate to create a four-stranded anti-parallel β-sheet. These interactions appear to be a major stabilizing force in the enzyme and contribute over 50% of the inter-subunit contacts and hydrogen bonds. Dimer formation generates not only the catalytic center, but also the extended substrate binding pocket.

Since viral proteolytic activity is essential for the generation of infectious virus particles in HIV and related retroviruses, therapeutic intervention for HIV-1 and HIV-2 has targeted the HIV protease. Small molecules have been developed as inhibitors and are currently undergoing clinical trials as antiviral agents. In clinical trials however, resistance to these inhibitors is being observed. Thus, new approaches for inhibiting retroviral proteases, in particular HIV-1 protease, are an important therapeutic goal in the treatment of retroviral infections. The present invention addresses these and other needs.

SUMMARY OF THE INVENTION

The present invention provides methods of inhibiting multimeric enzymes, in particular proteases, both in vivo and in vitro. The methods comprise contacting a first protease monomer with a second, defective protease monomer, such that the defective monomer and the first monomer form a dysfunctional multimeric protease. If the target protease is associated with a disease state, the step of contacting may be carried out by administering the defective monomer to a patient. For example, a gene encoding the defective monomer may be administered in a retroviral vector suitable for gene therapy.

In some embodiments, the defective monomer is a defective human immunodeficiency virus (HIV) protease monomer. For example, a defective HIV protease monomer may be one in which an active site aspartic acid is replaced by a second amino acid residue, such as arginine, lysine, asparagine and the like. Alternatively the defective HIV protease monomer may be a monomer fragment, e.g., residues 6–99 of the HIV protease monomer as shown in SEQ ID NO:1.

Thus, the invention also provides methods of inhibiting HIV replication in a mammalian cell. The method comprises introducing into the cell a recombinant construct comprising a promoter sequence operably linked to a polynucleotide encoding a defective HIV protease monomer. The target cell may be a human hematopoietic stem cell.

The invention further provides recombinant constructs comprising a promoter sequence operably linked to a polynucleotide encoding a defective protease monomer, such as a defective HIV protease monomer. The promoter sequence may be, for example, from an HIV LTR.

The constructs may be incorporated in retroviral vectors capable of infecting mammalian cells. The invention thus provides mammalian cells (e.g., human T cells) comprising a recombinant expression cassette including promoter sequences operably linked to a polynucleotide encoding a defective protease monomer.

Definitions

As used herein a "protease monomer" refers to a subunit of a multimeric protease that, when aggregated in the proper quaternary structure, results in the formation of an active protease.

As used herein the term "HIV protease monomer" refers to a monomer of approximately 99 amino acid residues, which results from autoprocessing of the HIV gag and gag/pol polyprotein precursors. The amino acid sequence and three-dimensional structure of an HIV protease monomer is described in Wlodawer et al. *Science* 245:616–621 (1989) as shown in SEQ ID NO:1.

A "defective protease monomer" is a mutated form of a protease monomer that is capable of forming a multimeric protease with one or more wild type monomers. The wild type monomers to which the defective monomer binds may be from the same or different proteases. Thus, the monomers of the invention can be used to inhibit the activity of a single protease or a family of related proteases. The multimeric protease so formed is dysfunctional, such that enzyme activity as determined in a standard assay for the particular protease is reduced by at least 50%, usually 75%, and preferably 90% or more, as compared to the wild-type multimeric enzyme.

A "defective HIV protease monomer" of the invention refers to an HIV protease monomer which, when present in an HIV-infected cell, forms a heterodimeric or homodimeric dysfunctional HIV protease and which substantially inhibits HIV protease activity in an infected cell. HIV protease activity can be determined using an in vitro assay that measures the rate of specific hydrolysis of the decapeptide ATLNFPISPW (SEQ ID NO:2), which corresponds to the sequence of the natural HIV-1 gag-pol polyprotein sequence from amino acid 151–160 and represents the junction between the protease and the reverse transcriptase. Cleavage occurs at the F-P bond. A suitable protocol for carrying out this assay is described in Babe et al. *Biochem*. 30:106–111 (1991). HIV protease activity is substantially inhibited if activity as measured in this assay is reduced by at least 50%, preferably 75%, and most preferably 95% or more.

As used herein a "polynucleotide encoding a defective protease monomer" is one which, when present in a cell, expresses a polypeptide which is or which comprises a defective protease monomer (e.g., HIV protease) of the invention. For example, the expressed polypeptide may be an isolated protease monomer or may be a polyprotein precursor (e.g., gag-pol) which is processed to produce the mature protease monomer.

In the expression of transgenes one of skill will recognize that the inserted polynucleotide sequence need not be identical and may be "substantially identical" to a sequence of the gene from which it was derived. For example, one of skill will recognize that because of codon degeneracy a number of polynucleotide sequences will encode the same polypeptide. These variants are specifically covered by the above term.

In addition, polynucleotides of the invention may encode polypeptides which are substantially identical to particular monomers disclosed here. Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing subsets of the two sequences over a "comparison window" to identify and analyze local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms. Preferred programs include BLAST, OWL, or GenPept, using standard parameters.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 70% sequence identity, preferably at least 80%, more preferably at least 90% and most preferably at least 95%, compared to a reference sequence using the programs described above (e.g., BLAST) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 70%, preferably at least 80%, more preferably at least 90%, and most preferably at least 95%.

Another indication that nucleotide sequences are substantially identical is if two molecules hybridize to each other under stringent conditions. Stringent conditions are sequence dependent and will be different in different circumstances. Generally, stringent conditions are selected to be about 50° C. lower than the thermal melting point (Tm) for the specific sequence at a defined ionic strength and pH. The Tm is the temperature (under defined ionic strength and pH) at which 50% of the target sequence hybridizes to a perfectly matched probe. The Tm of a hybrid, which is a function of both the length and the base composition of the probe, can be calculated using information provided in Sambrook, T. et al., (1989) *Molecular Cloning—A Laboratory Manual*, (2nd ed.) Vol. 1–3, Cold Spring Harbor Laboratory, Cold Spring. Typically, stringent conditions for a Southern blot protocol involve washing at 65° C. with 0.2×SSC.

Another indication that protein sequences are substantially identical is if one protein is specifically immunologically reactive with antibodies raised against the other protein. Under designated immunoassay conditions, specifically immunoreactive antibodies bind to a particular protein and do not bind in a significant amount to other proteins present in the sample. Specific binding to an antibody under such conditions may require an antibody that is selected for its specificity for a particular protein. For example, antibodies raised to defective HIV-1 protease monomers of the invention can be selected to obtain antibodies specifically immunoreactive with other defective monomers and not with other proteins. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

In the case of protease monomers of the invention, a modified protease monomer is substantially identical to a naturally occurring protease monomer if the modified protein is capable of binding the wild type monomer to form a heterodimer. Thus, modified proteins based on the monomers of the invention can be identified by assaying their ability to bind a wild type monomer to form a defective protease using assays described below.

The term "retroviral vector" as used herein means a vector that is derived from a retrovirus. Retroviral vectors may be constructed to have the capability to insert a gene or DNA fragment into the host chromosomal genome by a recombinational event, such that the DNA fragment may be stably expressed in the host cell. The basic design and use of retroviral vectors is described, for instance, in Singer, M. and Berg, P. Genes and Genomes, Mill Valley, Calif. (1991) pp. 310–314. A retrovirus is present in the RNA form in its viral capsid and forms a double-stranded DNA intermediate when it replicates in the host cell. Similarly, retroviral vectors are present in both RNA and double-stranded DNA forms, both of which forms are included in the term "retroviral vector".

The term "gene therapy" as used herein refers to a method of treating disease in an animal by introducing a nucleic acid (either RNA or DNA) into the cells of the animal. The nucleic acid introduced may be from the same species as the animal being treated or it may originate from another species. The nucleic acid may also be synthetically produced. The term includes introduction of nucleic acids into specific cells of the animal where the nucleic acids are subsequently expressed in the animal's cells and where the result of this expression is treatment of a disease.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

A "recombinant expression cassette" is a polynucleotide sequence containing a coding sequence which is capable of affecting expression of the coding sequence in hosts compatible with the sequence. Such cassettes include the coding sequence and regulatory sequences such as promoters, transcription termination signals as well as other sequences (e.g. enhancers) necessary or helpful in affecting expression.

DESCRIPTION OF THE PREFERRED EMBODIMENT

This invention involves the use of defective monomers to inhibit the activity of multimeric enzymes, in particular proteases. Such defective monomers can be used to inhibit the activity of a target enzyme either in vitro or in vivo, depending upon the particular application.

For example, defective viral protease monomers of the invention can be used to protect tissue culture cells from viral infection. Thus, mammalian or other cells grown in vitro for recombinant production of biologically important proteins can be protected from viral infection. Alternatively, human cells used in ex vivo therapies, such as T cells or other lymphocytes in adoptive immunotherapy can be protected using the methods of the invention. Typically, in vivo uses are directed toward treatment of a pathological condition associated with the protease activity.

Any of a number of multimeric enzymes, particularly proteases, can be targeted using the methods of the present invention. Examples include retroviral proteases, and the interleukin converting enzyme (ICE). Walker et al., *Cell* 78:343–352 (1994) and Wilson et al., *Nature* 370:270–275 (1994). Because the invention relates to a general method of inhibiting enzyme activity, the particular protease or other enzyme targeted is not critical to the invention.

The following discussion focuses on one embodiment of the invention, the inhibition of retroviral proteases. One of skill will recognize that this example is representative of other multimeric enzymes and that the methods described below can be used to inhibit activity of a number of multimeric enzymes, in particular proteases.

A preferred example of the use of defective monomers of retroviral proteases is the use of defective HIV (e.g., HIV-1 or HIV-2) protease monomers to interfere with viral maturation. The defective monomers result in the formation of inactive protease heterodimers or homodimers and thus inhibit the polyprotein processing events that are essential for viral maturation and infectivity. Because an enzymatic activity is being affected, a relatively low ratio of mutant to wild type genome is sufficient to produce a strong inhibition of the viral protease and a dramatic decrease in infectious virus titer.

In the present invention, intracellular immunization, whereby dominant negative mutants of viral gene products are expressed in relevant target cells, is used as means of specifically compromising viral replication (see, e.g., Feinberg et al. *Aids Res. and Human Retroviruses* 8, 1013–1022 (1992) and International Application No. PCT/US/01266). As explained below, this approach involves the introduction of a dominant negative mutant of HIV protease monomer into susceptible cells, preferably T cells or their progenitors.

I. Defective Monomers

Nucleotide sequences encoding the defective monomers of the invention can be readily designed and manufactured utilizing various recombinant DNA techniques well known to those skilled in the art. For example, the monomers can vary from the naturally-occurring sequence at the primary structure level by amino acid insertions, substitutions, deletions, and the like. These modifications can be used in a number of combinations to produce the final modified protein chain.

Polynucleotide sequences encoding proteases can be obtained from a number of sources. For instance, sequence information for various HIV strains and isolates are well known to those of skill in the art. The appropriate genes can be prepared from viral isolates using standard techniques. A gene encoding the HIV-1 strain SF-2 protease as part of a 179 amino acid fragment from the pol open reading frame is described in Babé et al. in *Protein and Pharmaceutical Engineering*, Craik et al. eds., pp71–88 (Wiley-Liss, New York, 1990). Similarly, sequences encoding an HIV-2 protease are described in Pichuantes et al. *J. Biol. Chem.* 265:13890–13898 (1990).

In general, modifications of the sequences encoding the defective monomers may be readily accomplished by a variety of well-known techniques, such as site-directed mutagenesis (see, Kunkel, *Proc. Natl. Acad. Sci. USA* 82:488–492 (1985); Gillman and Smith, Gene 8:81–97 (1979) and Roberts, S. et al., *Nature* 328:731–734 (1987)). The nucleotide sequences can be modified to yield desired polypeptides with a variety of properties, in addition to inhibition of protease activity. Examples include modifications to improve intracellular localization or targeting. In addition, monomers can be designed that form heterodimers with the wild type protein with higher affinity than either of the corresponding homodimers. In the case of retroviral proteases, point mutations can also be used to stabilize the protease to autolysis. (Rosé, et al., *J. Biol. Chem.* 268:11939–11945 (1993)). Such mutations are conveniently added to a defective monomer to increase its half-life in the cell.

Computer modelling studies can be used to design mutants with improved properties, such as having increased affinity for the wild type monomer. One of ordinary skill will appreciate that the effect of many mutations can easily be determined by routine screening and other methods.

In addition, the expected interactions between the wild type and mutant polypeptides can be investigated by in vitro assays. In the case of retroviral proteases, by increasing the amount of defective monomers, it is possible to increase the amount of mutant polyprotein incorporated into a budding virion. Theoretically, a 1 to 1 ratio of wild type monomer to defective monomer results in only 25% wild type protease, but 75% inactive protease. This dominant negative effect can be enhanced by increasing the amount of mutant genome present. For example, a 1:5 wild type to mutant ratio should result in only 3% wild type protease activity.

The particular form of the defective monomer used is not a critical aspect of the invention, so long as the monomer results in the formation of a substantially inactive protease multimers. For instance, various point mutations can be made in the protease monomer to provide monomers with improved properties. An example of a defective monomer having a point mutation is an HIV-1 protease in which the active site aspartic acid 25 is replaced with asparagine as illustrated in detail below. Other mutations at this site include substitutions of arginine, lysine, phenylalanine, or tryptophan. Other substitutions include replacing leucine 23 with lysine or tyrosine; replacing glycine 27 with phenylalanine or tryptophan; replacing glycine 49 with tryptophan; and replacing isoleucine 50 with tryptophan. One of skill will recognize that the above substitutions are merely illustrative and that various combinations of such mutations can also be used.

Other forms of defective monomers are fragments that block assembly of the protease. Thus, truncated monomers or peptides mimicking the interface of the protease monomers may be used to block dimerization. In the case of HIV proteases, polypeptide fragments comprising 50% or less of the complete sequence can be used so long as the fragment can serve as a scaffold for the dimer interface. Thus, oligopeptides mimicking the sequences from the antiparallel β sheet formed by the interdigitation of N-terminal and C-terminal residues of the protease monomers can be used (Babe, et al. Protein Sci. 1:1244–1253 (1992)). Such oligopeptides will typically consist of between about 5 residues and about 50 residues, usually between about 15 and about 30, preferably based on the carboxyl and amino terminal sequences of the monomers.

Larger fragments can also be used. For instance, monomers lacking the first 5 N-terminal residues can be used (Babé et al, *Biochem.* 30:106–11 (1991)). The larger fragments of the monomers will typically consist of about 60–80%, usually 90–95% of the primary structure of the monomer.

In addition to the recombinant techniques described above, defective monomers of the invention can be synthesized using standard techniques. Conveniently, they can be synthesized by conventional techniques employing automatic synthesizers, such as the Beckman, Applied Biosystems, or other commonly available peptide synthesizers using well known protocols. They can also be synthesized manually using techniques well known in the art. See, e.g. Stewart and Young, *Solid Phase Peptide Synthesis*, (Rockford, Ill., Pierce), 2d Ed. (1984).

II. Recombinant Constructs

Generally, the nomenclature used hereafter and the laboratory procedures in cell culture, molecular genetics, and nucleic acid chemistry described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. Much of the nomenclature and general laboratory procedures described below can be found in Sambrook, et al., *Molecular Cloning—A Laboratory Manual* (2nd Ed.), Vol. 1–3, Cold Spring Harbor Laboratory, Cold Spring Harbor, New York, 1989.

Methods for the preparation of vector constructs comprising appropriate expression cassettes and heterologous genes of interest are known to those of skill in the art. The nucleic acids used to make the constructs of the invention may be isolated from natural sources or may be synthesized in vitro. In general, oligonucleotides used in the methods of the invention can be chemically synthesized using, for instance, an Applied Bio Systems oligonucleotide synthesizer according to specifications provided by the manufacturer.

Typically, the sequence encoding the defective monomer is incorporated in an expression cassette and operably linked to appropriate expression regulatory sequences. In such constructs, the expression regulatory sequence is at least the minimal sequence required for efficient cell-specific expression, which generally is at least a promoter which is positioned in relation to the coding sequence to ensure efficient transcription. Frequently, sequences downstream of the promoter, especially intronic sequences, are included in the transgene constructs (Brinster et al. (1988) *Proc. Natl. Acad. Sci. USA* 85: 836. Usually the sequences upstream of the promoter are used contiguously, although various deletions and rearrangements can be employed. Some desired regulatory elements (e.g., enhancers, silencers) may be relatively position-insensitive, so that the regulatory element will function correctly even if positioned differently in a transgene than in the corresponding naturally occurring gene.

In the case of HIV proteases, suitable promoters for the invention include those derived from HIV LTRs, early SV40, CMV major late, adenovirus immediate early, histone H4, β-actin, MMTV, and HSV-TIC. In preferred embodiments, the polynucleotides of the invention are introduced into the target cells using retroviral vectors. In this case, the promoters in the retroviral long terminal repeat (LTR) can be used to drive expression. In the case of HIV proteases, T cells are the target cells in the methods of the invention, thus promoters known to be specific to these cells can also be used.

For targeting expression of the genes to HIV-infected cells regulatory sequences from HIV LTRs can be used to direct expression (see, International Application PCT/US90/01266). Only HIV-infected cells will comprise the transactivator gene (tat) required for activation of gene expression. Thus, gene expression will be primarily in infected cells.

To ensure efficient expression, 3' polyadenylation regions must be present to provide for proper maturation of the mRNA transcripts. The native 3'-untranslated region of the gene of interest is preferably used, but the polyadenylation signal from, for example, SV40, particularly including a splice site-which provides for more efficient expression, could also be used.

III. Gene Therapy

Any method for delivering the nucleic acids of the invention into the target cell can be used. A variety of methods have been disclosed in the prior art. Most research has focused on the use of retroviral and adenoviral vectors for gene delivery into the cell. For gene therapy to be practicable, it is desirable to employ a DNA transfer method that is capable of directing the desired polynucleotides into specific target cell types (e.g., T cells or their progenitors) and is highly efficient in mediating uptake of the therapeutic polynucleotide into the target cell population.

Retroviral vectors are the most commonly used vectors for transducing human cells in gene therapy protocols (see, e.g., Miller et al. *Mol. Cell. Biol.* 10:4239 (1990); Kolberg J. NIH Res. 4:43 (1992); Cornetta et al. *Hum. Gene Ther.* 2:215 (1991)). The major advantages of retroviral vectors for gene therapy are the high efficiency of gene transfer into replicating cells, the precise integration of the transferred genes into cellular DNA, and the lack of further spread of the sequences after gene transduction.

Adenoviral vectors have also been described for potential use in human gene therapy (Rosenfeld et al. *Cell* 68:143 (1992)). Major advantages of adenovirus vectors are their potential to carry larger insert polynucleotide sequences than retroviral vectors, very high viral titre, ability to infect non-replicating cells, and suitability for infecting tissues in situ, especially in the lung.

Another gene transfer method that has been approved for use in humans is physical transfer of plasmid DNA in liposomes directly into tumor cells in situ. Unlike viral vectors which must be propagated in cultured cells, plasmid DNA can be purified to homogeneity and thus reduces the potential for pathogenic contamination. Liposome-mediated DNA transfer has been described by various investigators (see, e.g., Litzinger and Huang *Biochem. Biophys. Acta* 1113:201 (1992); Felgner W091/17424; W091/16024).

Since the majority of the approved gene transfer trials in the United States rely on replication-defective retroviral vectors, production and use of such vectors is described in more detail below. It will be understood, however, that the particular method used to introduce the polynucleotides of the invention into the target cells is not a critical aspect of the invention.

Retroviral vectors are produced by genetically manipulating retroviruses. The wild type retroviral genome and the proviral DNA have three genes: the gag, the pol and the env genes, which are flanked by two long terminal repeat (LTR) sequences. The gag gene encodes the internal structural (nucleocapsid and capsid) proteins; the pol gene encodes the RNA directed DNA polymerase (reverse transcriptase) as well as protease and integrase; and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsidation of viral RNA into particles (the Psi site). See Mulligan, R. C., In: Experimental Manipulation of Gene Expression, M. Inouye (ed), 155–173 (1983); Mann, R., et al., *Cell*, 33:153–159 (1983); Cone, R. D. and R. C. Mulligan, *Proceedings of the National Academy of Sciences, U.S.A.*, 81:6349–6353 (1984).

The design of retroviral vectors is well known to one of skill in the art. Typically, retroviral vectors are produced when a defective viral genome is introduced into a packaging cell line. A packaging cell line is a genetically constructed mammalian tissue culture cell line that produces the necessary viral structural proteins required for packaging, but which is incapable of producing infectious virions. The defective genomes, on the other hand, lack the structural genes but contain the sequences required for integration into the target cell genome, for packaging of the genome into infectious virions, as well as those sequences required for expression of the desired polynucleotide. Thus, transfecting defective genomes into packaging cell lines results in the production of retroviral vector particles with the desired genetic construction. Preparation of retroviral vectors and their uses are described in many publications including European Patent Application EPA 0 178 220, U.S. Pat. No. 4,405,712, Gilboa, *Biotechniques* 4:504–512 (1986), Mann, et al., *Cell* 33:153–159 (1983), Cone and Mulligan, *Proc. Natl. Acad. Sci. USA* 81:6349–6353 (1984), Eglitis, M. A, et al. (1988) *Biotechniques* 6:608–614, Miller, A. D. et al. (1989) *Biotechniques* 7:981–990, Miller, A. D. (1992) Nature, supra, Mulligan, R. C. (1993), supra. and Gould, B. et al., and International Patent Application No. WO 92/07943 entitled "Retroviral Vectors Useful in Gene Therapy".

To prepare a packaging cell line, an infectious clone of a desired retrovirus, in which the packaging site has been deleted, is constructed. Cells comprising this construct will express all structural proteins but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13. See Miller et al., *J. Virol.* 65:2220–2224 (1991). Examples of other packaging cell lines are described in Cone, R. and Mulligan, R. C., *Proceedings of the National Academy of Sciences, USA*, 81:6349–6353 (1984) and in Danos, O. and R. C. *Mulligan, Proceedings of the National Academy of Sciences, USA*, 85: 6460–6464 (1988). In addition, Carroll et al. J. Virol. 68:6047–6051 (1994) describe stable human immunodeficiency virus (HIV) packaging cell lines that when transfected with an HIV-based retroviral vector produce packaged vectors capable of transducing susceptible CD4(+) cells.

Most gene therapy protocols involve treating cells from the patient ex vivo and then reintroducing the cells into the patient. For example, to target T cells susceptible to HIV-infection, bone marrow derived hematopoietic stem cells from an infected patient are used. The viral infection of other cells is eliminated in the host, followed by autologous hematopoietic reconstitution through transplantation of genetically modified stem cells.

Significant progress has been made in isolating and transducing stem cells. A number of recent reports describe techniques suitable for isolating human hematopoietic stem cells (see, e.g., Baum et al. *Proc. Natl. Acad. Sci. USA* 89:2804–2808 (1992)). Generally, these methods rely on the presence of a cell surface antigen, CD34, which is used as a marker for hematopoietic stem cell populations. In addition, Xu et al. *Exp. Hematol.* 22:223–230 (1994) report transduction of CD34+ cells isolated from Gaucher patients.

Delivery of sequences encoding defective HIV protease monomers may also be accomplished in vivo by administration of the retroviral vector particle complexes. Typically this is done by systemic administration to a patient (e.g., intravenous, intraperitoneal, intramuscular, subdermal, or intracranial infusion). For systemic administration, injection is preferred, including intramuscular, intravenous, intraperitoneal, and subcutaneous injection. Suitable formulations for injection are found in Remington's Pharmaceutical Sciences, Mack Publishing Company, Philadelphia, PA, 17th ed. (1985). A variety of pharmaceutical compositions can be prepared. The pharmaceutical compositions are suitable in a variety of drug delivery systems. For a brief review of present methods of drug delivery, See, Langer, *Science* 249:1527–1533 (1990).

IV. Pharmaceutical Compositions

The defective monomers of the invention can also be administered directly to inhibit protease activity in a patient. Thus, pharmaceutical compositions suitable for use in a variety of drug delivery systems can be prepared. Suitable formulations for use in the present invention are found in *Remington's Pharmaceutical Sciences*, Mack Publishing Company, Philadelphia, Pa., 17th ed. (1985).

The defective monomers may be prepared as formulations in pharmaceutically acceptable media, for example saline, PBS, and glucose, generally at a therapeutically effective dose, the concentrations of which will be determined empirically in accordance with conventional procedures for the particular purpose. The additives may include bactericidal agents, stabilizers, buffers, or the like.

In order to enhance serum half-life, the monomers may be encapsulated, introduced into the lumen of liposomes, prepared as a colloid, or other conventional technique may be employed which provides an extended serum half-life of the peptides. A variety of methods are available for preparing liposomes, as described in, e.g., Szoka et al., *Ann. Rev. Biophys. Bioeng.* 9:467 (1980); Szoka, *Liposomal Drug Delivery*, in *Membrane Fusion*, Wilschut and Hoekstra eds. (Marcel Dekker, Inc. New York, 1991); and U.S. Pat. Nos. 4, 235,871 4,501,728 and 4,837,028.

In many cases, the defective monomers will be used to inhibit intracellular enzyme activity. Thus, defective monomers of the invention are preferably administered such that they are delivered intracellularly. For instance, targeting moieties which specifically interact with cell surface proteins on a desired cell population (e.g., T cells) can be used to target the defective monomers to the cells. The monomers are then delivered to the intracellular space by receptor-mediated endocytosis.

Alternatively, liposomes bearing the targeting moiety can be used to deliver the defective monomers to the target cell population. Targeting of liposomes using a variety of targeting agents (e.g., ligands, receptors and monoclonal antibodies) is well known in the art. (see, e.g., U.S. Pat. Nos. 4,957,773 and 4,603,044). Once adsorbed to the target cell, the contents of the liposomes are delivered to the intracellular space by a number of mechanisms, such as endocytosis, exchange of lipids with the cell membrane, or fusion of the liposome with the cell membrane.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient.

The pharmaceutical compositions are intended for parenteral, topical, oral or local administration, such as by aerosol or transdermally, for prophylactic and/or therapeutic treatment. Commonly, the pharmaceutical compositions are administered parenterally, e.g., intravenously. Thus, the invention provides compositions for parenteral administration which comprise a defective monomer dissolved or suspended in an acceptable carrier, preferably an aqueous carrier, e.g., water, buffered water, 0.4% saline, 0.3% glycine, hyaluronic acid and the like. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

EXAMPLES

This example describes the construction and use of recombinant vectors encoding defective protease monomers of the invention. These mutants maintain the structural features of the wild type enzyme, but the catalytic site region is modified, resulting in dimeric aspartyl proteases with reduced activity.

Three mutants were made in the active site region of the dimeric aspartyl protease that resulted in reduced proteolytic activity: A28S, which has been characterized previously (Co et al., *Biochemistry* 33:1248–1254. (1994) and Ido et al., *J. Biol. Chem.* 266:24359–24366 (1991)); T26S, which mimics a substitution found in the Rous sarcoma virus protease (Grinde, et al., *J. Biol. Chem.* 267:9481–9490 (1992)); and D25N, in which activity is abolished by mutation of the catalytic aspartic acid residues (Kohl, et al., *Proc. Natl. Acad. Sci. U.S.A.* 85:4686–4690 (1988)). These variant enzymes all carried the mutation Q7K, which stabilizes the protease to autoproteolysis (Rose et al., *J. Biol. Chem.* 268:11939–11945 (1993)).

A bicistronic expression vector was developed for the production in *E. coli* of mutant proteases with reduced activity. The vector permitted the heterologous expression of inactive forms of the protease that were otherwise incapable of autoprocessing from precursor protein constructions. Kinetic analysis of the purified variant proteases was performed using a peptide substrate whose sequence is derived from the protease-reverse transcriptase junction. This peptide is representative of the cleavage sites in the viral polyprotein (Tomasselli, et al., *J. Biol. Chem.* 265:14675–14683 (1990)). Briefly, the experiments were carried out as follows. Protease activity was measured by the method of Pichuantes et al., *J. Biol. Chem.* 265:13890–13898 (1990). Samples were incubated in activity buffer (50 mM sodium acetate, pH 5.5, 1 M NaCl, 1 mM DTT, 1 mM EDTA) in the presence of the decapeptide substrate $NH_2$-ATLNFPISPW-COOH (SEQ ID NO:2). Cleavage products were separated by reversed-phase HPLC. Purified protein concentrations were determined by active site titration using inhibitor U85548 (a gift of Dr. A. Tomasselli, Upjohn Laboratories). The kinetic parameters obtained are shown in Table I.

TABLE I

| mutant | $k_{cat}$ (min$^{-1}$) | $K_M$ ($\mu$M) | $k_{cat}/K_M$ (min$^{-1}\mu$M$^{-1}$) |
| --- | --- | --- | --- |
| WT | 820 ± 20 | 990 ± 50 | 0.82 ± 0.04 |
| Q7K | 1030 ± 30 | 1300 ± 60 | 0.81 ± 0.03 |
| Q7K, T26S | 240 ± 10 | 900 ± 60 | 0.26 ± 0.02 |
| Q7K, A28S | 17 ± 2 | 1100 ± 140 | 0.015 ± 0.003 |
| Q7K, D25N | 0 | 0 | 0 |

The presence of serines in the active site of HIV-1 protease at positions 26 and 28 had insignificant effects on the binding of substrate ($K_M$) but a dramatic effect on substrate turnover ($k_{cat}$) The T26S mutation decreased $k_{cat}$ by approximately 4-fold, whereas the $k_{cat}$ of A28S was decreased by nearly 50-fold when compared against the wild type enzyme. No measurable activity was exhibited by the protease in which the active site aspartate (D25) was replaced by asparagine.

The structures of the Q7K T26S and Q7K A28S enzymes complexed with the nonpeptide inhibitor UCSF-8 (Rutenber, et al., *J. Biol. Chem.* 268:15343–15346 (1993)) were determined by X-ray crystallography to a resolution of 2.1 A. Comparison with the structure of the Q7K enzyme identified no significant deviations in the conformation of the residues in the binding pockets of the mutant enzymes, further suggesting that the mutations would not affect substrate binding.

To assess the effect of reduced proteolytic activity on viral polyprotein processing, the mutants were introduced into a tissue culture system for analyzing HIV virion assembly. Protease genes containing the three single mutations T26S, A28S, and D25N were cloned into a HIV-gpt vector as described by Page et al., *J. Virol.* 464:5270–5276 (1990). This vector encodes all of the HIV-1 HXB-2 viral proteins except for envelope, and when transfected into mammalian cells produces assembled viral capsids. To do this, 30 $\mu$g of plasmid DNAs containing the wild type or mutant proteases were transfected into COS-7 cells using the standard calcium phosphate protocol (Graham and van der Eb, *J. Virol.* 63:2527–2533 (1973)). For labeling of transient expression products, cells were grown for approximately 48 hours after transfection. Cells were starved for 20 minutes in DMEM deficient in methionine, supplemented with 2% dialyzed fetal calf serum. Cells were labeled for 6 hours using 0.1 mCi/ml of [$^{35}$S] Translabel (ICN, 70% methionine/30% cysteine, 1000 Ci/mmol specific activity) in 4 mL of DMEM deficient in methionine and supplemented with 2% dialyzed fetal calf serum, followed by a 6 hour cold chase in complete media. Capsids were isolated by sucrose cushion sedimentation as described by Page et al., supra, and precipitated by treatment with trichloroacetic acid. Proteins were analyzed by 12.5% SDS-polyacrylamide gel electrophoresis and visualized by autoradiography according to standard techniques.

The presence of the T26S, A28S, and D25N protease mutations had a dramatic effect on the degree to which viral polyproteins were processed. After a 12 hour pulse-chase, wild type virions contain predominantly mature capsid protein (p24), with a small amount of a less mature form (p25). In T26S PR capsids, the capsid protein exists largely in the p25 form, and additional precursors are visible at 39 and 55 kDa. The A28S PR and D25N PR capsids do not show any significant processing and contain immature p55$^{gag}$ precursor almost exclusively. Small amounts of processing intermediates could be observed in A28S PR samples only after extended periods of time.

Longer time periods were necessary to examine the ability of the less active proteases to process viral capsids. Accumulation of mature capsid protein was followed over 130 hours. For these experiments, COS-7 cells were transfected with 30 $\mu$g of plasmid DNA and culture supernatants harvested at 24, 48, 72, 100, and 130 hours post transfection. Supernatants were filtered through 0.45 micron filters and viral particles purified as described by Page et al., supra. Purified viral particles were disrupted with 1% Triton and p24 levels of three serial dilutions measured by ELISA (NEN/DuPont).

Although the T26S PR particles display a short lag relative to WT HIV-gpt, significant levels of p24 were present in particles at later time points. Only low levels of p24 were present in cells transfected with the A28S PR clone, indicating that processing of polyprotein precursors is dramatically diminished even after 130 hours. The order of appearance of gag processing intermediates in the T26S PR and A28S PR capsids over longer time periods was similar to the order in which they have been observed in other systems, suggesting that selection of cleavage sites has not been altered in mutant capsids. The magnitude of the processing defect in virions is approximately correlated with the diminished $k_{cat}$ values measured in vitro. It was noted that larger amounts of p24 were present in T26S PR capsid samples than WT samples at later time points. It has been reported previously that HIV capsids are more stable when immature than when processed (Park and Morrow, *Virology* 194:843–850. (1993)). The detection of more particle-associated p24 in T26S PR samples than WT may reflect the initial accumulation of more immature or partially processed particles, which then are further processed and detected in the assay.

The effect of altered kinetics of polyprotein processing on viral infectivity was analyzed. Infectious particles were generated by co-transfecting the wild type and mutant-bearing HIV-gpt vectors with an HIV-1 HXB-2 envelope-expressing plasmid, HXB-2 env described by Page et al., supra. Briefly, media from COS-7 cells transfected with 30 $\mu$g HIV-gpt and 70 $\mu$g of HXB2-env were harvested at 48 hrs post transfection. 75, 250, and 750 $\mu$l of media were incubated with HeLaT4 indicator cells for 1 hour, followed by addition of 1 ml of fresh media. After 24 hours drug selection was started by addition of DMEM containing 10% fetal calf serum, 50 µg/ml mycophenolic acid, 14 µg/ml xanthine, and 250 µg/ml hypoxanthine. Colonies were fixed and stained with 0.5% crystal violet. For normalization of data to total particle levels, purified particles were disrupted with 0.1% Triton-X100, 5 mM EDTA and digested with exogenous purified HIV-1 protease. Total p24 in digested samples was determined by p24 ELISA and the colony numbers divided by the ratio of mutant to wild type p24 levels to generate HeLaT4 colonies/ml/unit p24. Samples from four independent transfections were analyzed at 48 hours and gave the results shown in Table II.

TABLE II

| experiment | HeLaT4 colonies/ml/unit p24 | | | |
|---|---|---|---|---|
| | WT | T26S | A28S | D25N |
| #1 | 400 ± 15 | 131 ± 7 | 0 | 0 |
| #2 | 176 ± 8 | 64 ± 5 | 0 | 0 |
| #3 | 121 ± 11 | 31 ± 5 | 0 | 0 |
| #4 | 106 ± 5 | 40 ± 3 | 0 | 0 |

At a point where p24 levels are approximately equal between WT and T26S PR virions, the T26S PR clones are consistently 3–4 fold less infectious than wild type. A28S PR and D25N PR clones produced no infectious particles at this time point or later time points up to 130 hours (data not shown). The data suggest that a 4-fold reduction in proteolytic activity still permits polyprotein processing within a time in which the virus is potentially viable. When processing proceeds at a 50-fold slower rate, however, the virus does not mature within this window and infectious virions are not produced.

Figure 1:
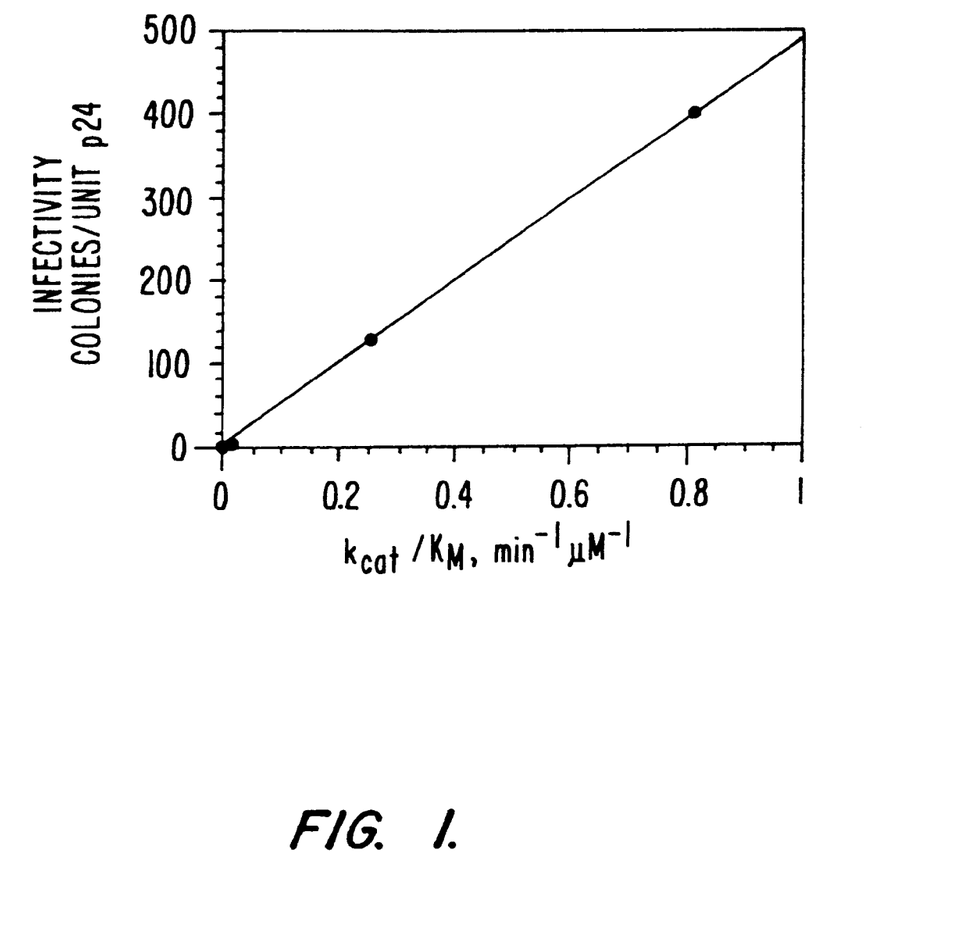
FIG. 1 shows the relationship of $k_{cat}/K_M$ and infectivity for protease mutants and mutant containing virions.

These data suggest that there is a direct correlation between the activity of the protease, as measured by the efficiency constant ($k_{cat}/K_M$), and the infectivity of the virus (FIG. 1). There is a clear effect of the mutants on both the rate of polyprotein processing, as determined by quantitation of particle associated p24 in transfected cell supernatants, and the rate at which infectious particles are produced. The T26S PR virions, in which only 25% of the total wild type protease activity is present, are still able to infect cells, despite a decreased rate of processing. The difference in relative infectivities between the wild type and T26S PR virions at 48 hours probably reflects a decreased number of fully processed virions present in the T26S PR population, although it is unclear if partially processed virions are infectious. In the case of the A28S PR capsid samples, processing of the capsid antigen reached only minimal levels by 48 hours. It is likely that the absence of infectious articles in the assay is due to the very small number, or absence, of particles which are processed adequately to be infectious.

These data support the concept that a minimal amount of active viral protease is required during the maturation process in order to yield infectious particles. Protease activity below this threshold level leads to irreversibly immature and non-infectious virions.

Figure 2A:
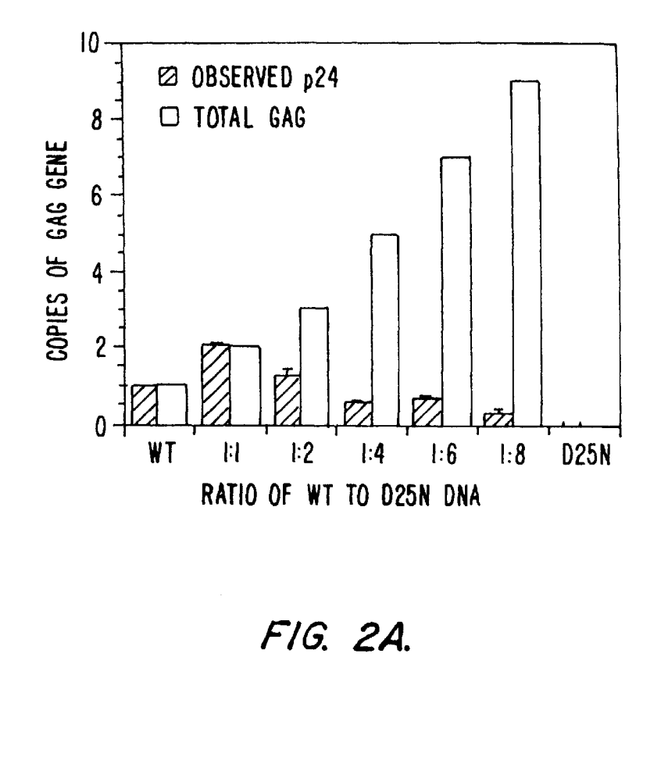
FIGS. 2A and 2B show the results of an experiment in which the amount of gene encoding a defective monomer was increased from 0 to 8-fold over the concentration of the wild type genome.
Figure 2B:
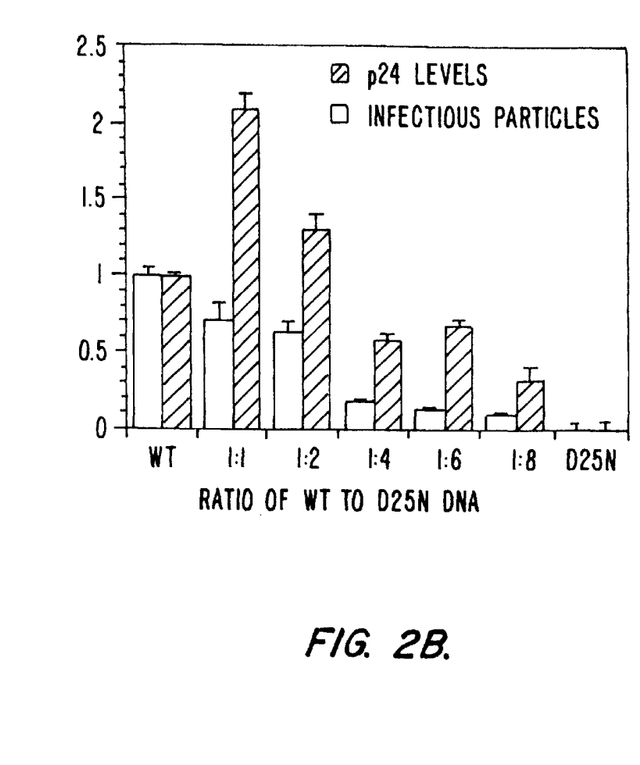

The effect of adding increasing amounts of mutant genomes in the presence of a fixed level of wild type was also examined. By including the envelope-producing plasmid HXB2-env, it is possible to generate HIV-1 virions which are capable of infecting a marker cell line, HeLaT4 as described by Page et al., supra. Virions released from the transfected cells were also harvested by sucrose gradient centrifugation for component characterization as described above. From the combination of these assays it is possible to relate the amount of correctly processed p24 to the number of infectious particles as a function of the amount of pHIVD25N-gpt used in the experiment. FIGS. 2A and 2B show the results of an experiment where the amount of mutant genome (D25N) was increased from 0 to 8-fold over the concentration of the wild type genome. A reduction of protease activity was seen by the reduced levels of p24 and increased levels of immature gag protein relative to cells containing the wild type gene (FIG. 2A). The dominant negative phenotype was observed in the consistent reduction in the number of infectious particles associated with increased levels of D25N (FIG. 2B). These results show that by decreasing the amount of mutant genome in a cell 6-fold over the wild type level it is possible to reduce protease activity enough to prevent maturation of 90% of the viral particles produced by the cell.

Figure 3A:
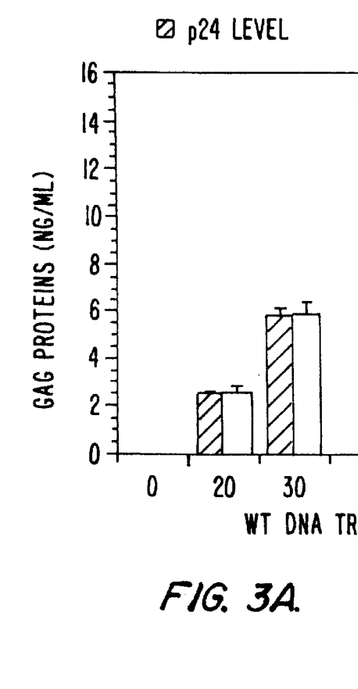
FIGS. 3A–D shows the results of an experiment in which wild type HIV-gpt DNA was transfected into COS-7 cells (3A, 3C) or a COS-7 derivative cell line stably expressing the viral polyprotein containing a D25N mutant of the protease (3B, 3D). Polyprotein processing (p24 v. total gag) (3A, 3C) and infectivity (3B, 3D) were examined.
Figure 3B:
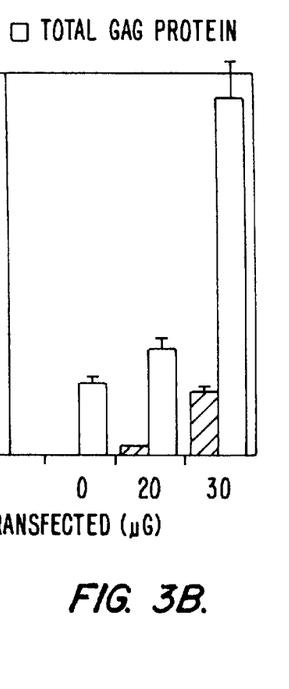
Figure 3C:
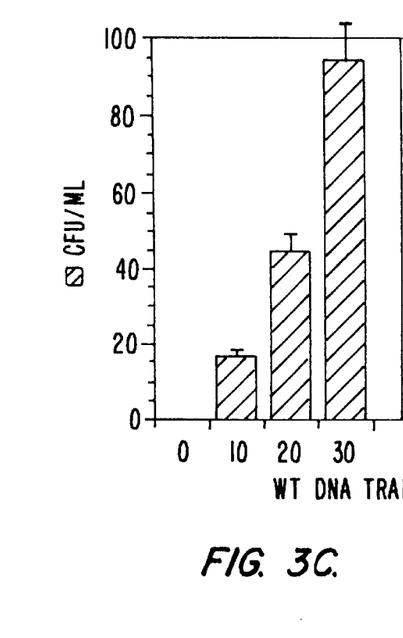
Figure 3D:
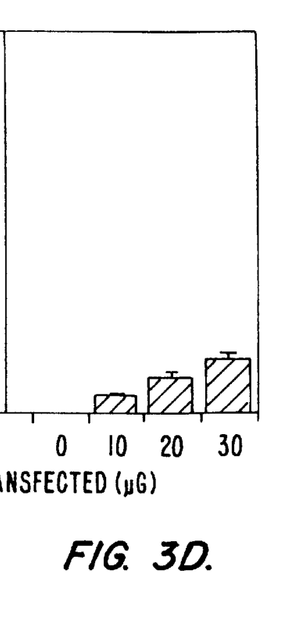

The effect of stably expressing a viral polyprotein containing the D25N protease mutation was also examined. Cells were transfected with pHIVD25N-gpt and selected for the presence of the drug resistance marker. A clone (12A2) was isolated which stably expressed the HIV-1 proteins, and from which immature viral capsids were released. The 12A2 cell line was transfected with HXB-2 env and varying amounts of wild type HIV-gpt DNA, and compared next to the parent cells. Capsid processing (FIGS. 3A and 3B) and particle infectivity (FIGS. 3C 3D) were examined. As shown in FIG. 3A, transfection of the parental cells yielded mature particles, in which all gag protein had been processed to p24. The 12A2 cell line, on the other hand, produced viral particles which contained very little p24, but large amounts of immature gag (FIG. 3B). The 12A2 cell line (FIG. 3D) produced approximately 5-fold fewer infectious particles than the parental cell line (FIG. 3C) when transfected with equivalent amounts of DNA.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of inhibiting HIV protease activity in a mammalian cell susceptible of HIV infection, the method comprising contacting the cell or its progenitor in cell culture with a nucleic acid construct comprising a promoter sequence operably linked to a polynucleotide encoding a defective HIV protease monomer as shown in SEQ ID NO: 1 except the aspartic acid residue at position 25 is replaced by lysine, such that the defective protease monomer is expressed in the cell and dysfunctional HIV proteases are formed in the cell, thereby inhibiting HIV protease activity in the cell.

2. A method of inhibiting HIV protease activity in a mammalian cell susceptible of HIV infection, the method comprising contacting the cell or its progenitor in cell culture with a nucleic acid construct comprising a promoter sequence operably linked to a polynucleotide encoding a defective HIV protease monomer as shown in SEQ ID NO: 1 except the aspartic acid residue at position 25 is replaced by lysine, the glycine residue at position 49 is replaced by tryptophan, and the isoleucine at position 50 is replaced by tryptophan, such that the defective protease monomer is expressed in the cell and dysfunctional HIV proteases are formed in the cell, thereby inhibiting HIV protease activity in the cell.

3. A recombinant construct comprising a promoter sequence operably linked to a polynucleotide encoding a defective protease monomer from human immunodeficiency virus (HIV) wherein the defective HIV protease monomer is as shown in SEQ ID NO: 1 except the aspartic acid residue at position 25 is replaced by lysine.

4. A recombinant construct comprising a promoter sequence operably linked to a polynucleotide encoding a defective protease monomer from human immunodeficiency virus (HIV) wherein the defective HIV protease monomer is as shown in SEQ ID NO: 1 except the aspartic acid residue at position 25 is replaced by lysine, the glycine residue at position 49 is replaced by tryptophan, and the isoleucine at position 50 is replaced by tryptophan.

5. A retroviral vector that will infect a mammalian cell, the retroviral vector comprising a promoter sequence operably linked to a polynucleotide encoding a defective protease monomer from human immunodeficiency virus (HIV) wherein the defective HIV protease monomer is as shown in SEQ ID NO: 1 except the aspartic acid residue at position 25 is replaced by lysine.

6. A retroviral vector that will infect a mammalian cell, the retroviral vector comprising a promoter sequence operably linked to a polynucleotide encoding a defective protease monomer from human immunodeficiency virus (HIV) wherein the defective HIV protease monomer is as shown in SEQ ID NO: 1 except the aspartic acid residue at position 25 is replaced by lysine, the glycine residue at position 49 is replaced by tryptophan, and the isoleucine at position 50 is replaced by tryptophan.

* * * * *

UNITED STATES PATENT AND TRADEMARK OFFICE
CERTIFICATE OF CORRECTION

PATENT NO. : 6,165,794
DATED : December 26, 2000
INVENTOR(S) : Craik et al.

It is certified that error appears in the above-identified patent and that said Letters Patent is hereby corrected as shown below:

Column 1,
Line 4, insert:
-- STATEMENT AS TO RIGHTS TO INVENTIONS MADE UNDER FEDERALLY SPONSORED RESEARCH AND DEVELOPMENT --
 -- This invention was made with Government support under Grant No. GM39952, awarded by the National Institutes of Health. The Government has certain rights in this invention. --

Signed and Sealed this

Twelfth Day of March, 2002

Attest:

Attesting Officer

JAMES E. ROGAN
Director of the United States Patent and Trademark Office